United States Patent [19]

Mehl et al.

[11] 4,116,066
[45] Sep. 26, 1978

[54] SPECIMEN SAMPLER CUP

[75] Inventors: Jack J. Mehl, Landing; Edward L. Nugent, North Caldwell, both of N.J.

[73] Assignee: Becton, Dickinson and Company, Rutherford, N.J.

[21] Appl. No.: 859,591

[22] Filed: Dec. 12, 1977

[51] Int. Cl.² .............................................. A61B 10/00
[52] U.S. Cl. ............................... 73/421 R; 73/425.6; 128/2 F
[58] Field of Search ..................... 73/421 A, 425.6; 128/2 F

[56] References Cited

U.S. PATENT DOCUMENTS

| | | | |
|---|---|---|---|
| 3,494,351 | 2/1970 | Horn | 128/2 F |
| 3,894,845 | 7/1975 | McDonald | 128/2 F |
| 3,947,251 | 3/1976 | Quame | 73/421 R |
| 4,063,460 | 12/1977 | Svensson | 73/425.6 |

*Primary Examiner*—S. Clement Swisher
*Attorney, Agent, or Firm*—Kane, Dalsimer, Kane, Sullivan & Kurucz

[57] ABSTRACT

A device for the collection of a liquid, such as urine, which provides efficient means for both collecting the liquid and transferring it to a tube for storage. A collection container is provided with a hollow cannula attached to its bottom. The cannula is slotted near its base, and serves as the conduit through which liquid may be transferred from the container to an evacuated tube. When the stopper of such a tube is punctured by the cannula, the pressure difference causes liquid deposited in the receptacle to be drawn through the slot, the hollow cannula, and into the tube.

15 Claims, 7 Drawing Figures

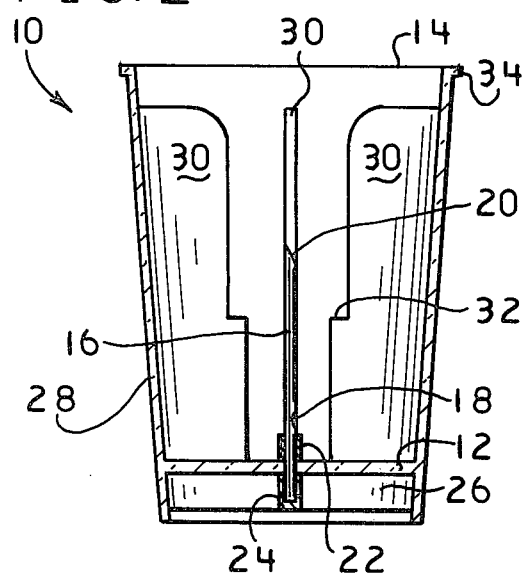
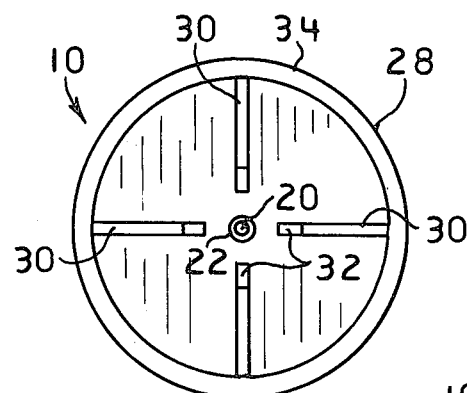
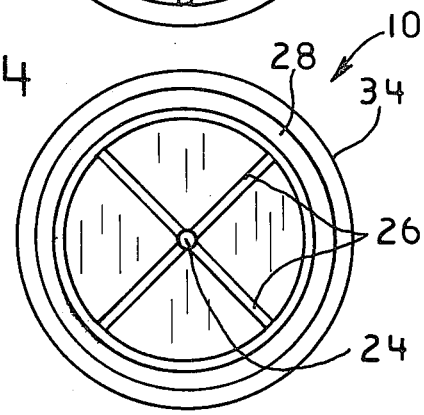
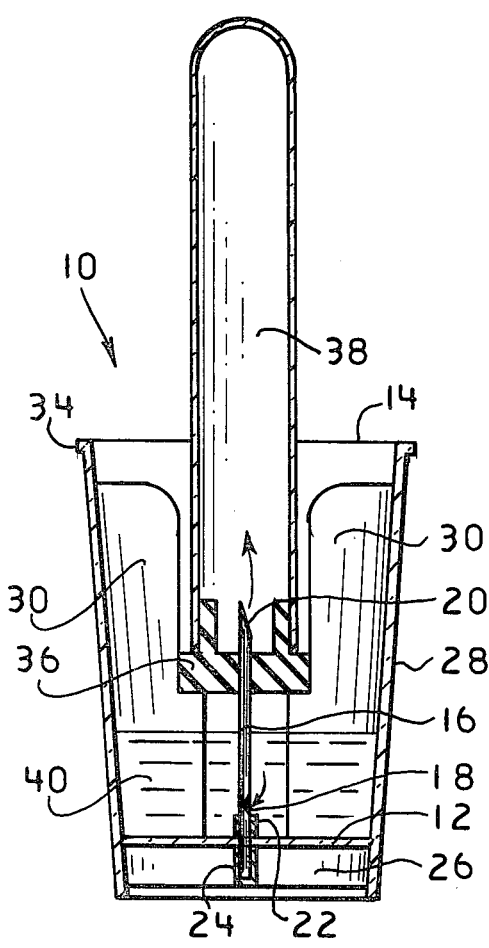
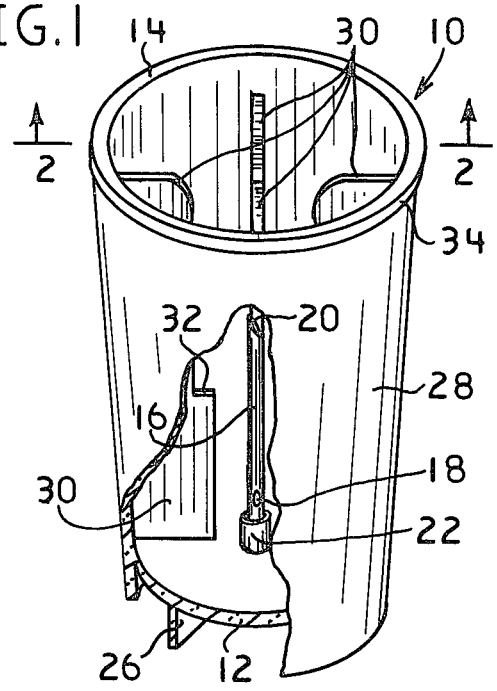

SPECIMEN SAMPLER CUP

BACKGROUND OF THE INVENTION

This invention concerns specimen sampler cups or containers for collection and storage of liquid specimens, such as urine. A slotted hollow cannula is incorporated within the container to serve as a conduit through which liquid may be drawn into a tube for storage or testing. When the stopper or an evacuated tube is penetrated by the cannula, liquid is drawn through the slot and into the tube.

Transfer of a liquid from a collection well to a container more suitable for storage under sterile conditions has not been satisfactorily accomplished to date. Receptacles into which liquid samples are deposited shoud typically have large mouths to prevent soiling of both the patent and the outside of the container. However, transfer of liquid from such a container to a smaller one, such as a test tube, can be difficult to accomplish without any spillage. Even if a funnel is used, there is the problem of contamination due to overflow of the tube. These problems are mulitplied if a plurality of tubes are to be filled with the sample from the collection well.

SUMMARY OF THE INVENTION

It is an object of the invention to provide an apparatus for collecting a liquiid sample from which the liquid may be quickly and efficiently transferred to an evacuated container. This is accomplished by employing a collection container which has a hollow cannula mounted thereon. The cannula is mounted in such a position that its top end and associated openig may easily be used to penetrate the interior of an evacuated container when the latter is pressed upon it. An opening near the base of the cannula establishes flow communication between the interior of the cannula and the collection container.

In use, the liquid specimen is deposited in the collection container to a level where at least the lower opening of the cannula is covered. A second, evacuated container having a resilient closure is placed in such a position that this closure is pierced by the top end of the cannula. The pressure differential created by the vacuum and the atmospheric pressure will cause the liquid to move through the lower opening, the hollow cannula, and through the upper opening into the second container. This eliminates the need for collecting specimens into a second vessel and then aspirating into an evacuated container, which is an object of the invention.

The apparatus also eliminates any possibility of spillage or contamination during transfer of the liquid, which is another object of the invention.

Still another object of the invention is to provide a specimen sampling apparatus which is simple to manufacture under sterile conditions and can be packaged individually.

Further objects and uses of the invention will become apparent from the detailed description which follows.

BRIEF DESCRIPTION OF THE DRAWINGS

FIG. 1 is a partially cutaway perspective view of the invention;

FIG. 2 is a sectional elevational view of the invention;

FIG. 3 is a top view of the invention;

FIG. 4 is a bottom view of the invention;

FIG. 5 is a sectional elevational view of the invention as utilized in conjunction with an evacuated tube;

DETAILED DESCRIPTION OF THE INVENTION

Figure 6:
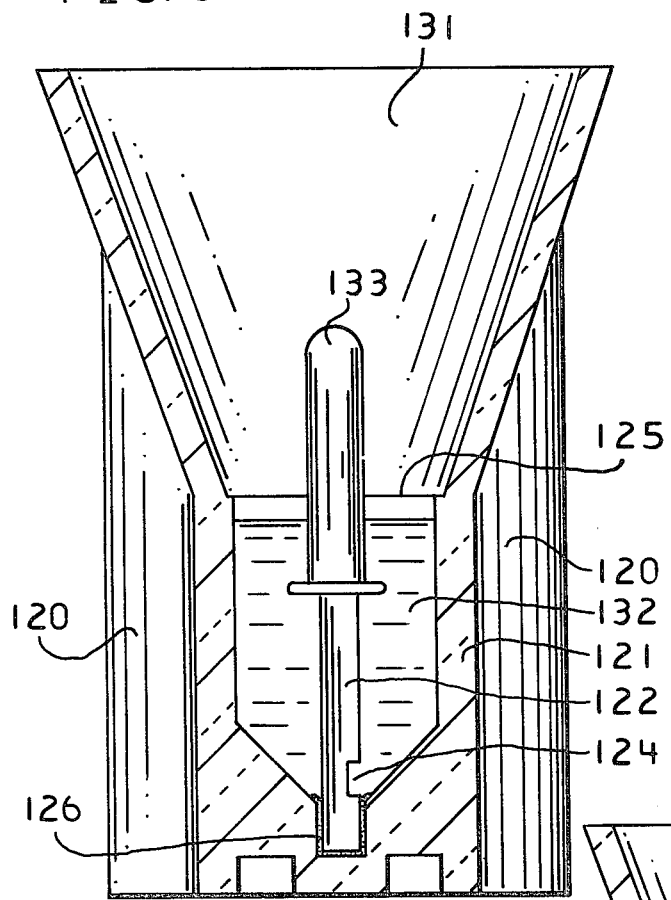
FIG. 6 is a sectional elevation view of another embodiment of the invention.

FIGS. 1–4 illustrate the specimen sampler cup 10 in detail. The cup is tapered in the direction of its closed, bottom end 12, and thereby provides a relatively wide mouth 14 at the upper end.

A cannula 16 extends from the bottom end of the cup, and has a slot 18 near its lower end. The cannula has a pointed tip 20 adapted for penetration of a resilient closure 36 of an evacuated container 38. The needle is supported by two hub sections 22 and 24; the former extends upwardly from the bottom end 12, and the latter protrudes below this end. The lower hub 24 is supported by ribs 26 extending between the hub and the side wall 28 of the cup. The cannula may be secured by epoxy or any other conventional means.

The cup also contains ribs 30 which are attached to the side walls 28 of the cup as well as the bottom surface 12. These ribs have shoulder portions 32 at a point below the tip of the cannula. The upper portion of the wall 28 terminates in a flange 34 to facilitate handling of the cup.

FIG. 5 illustrates the operation of the invention. After the cup has been filled with a liquid specimen 40, an evacuated tube 38 having a resilient closure 36 (such as a rubber stopper) is inserted within the cup. The ribs 30 serve to center and guide the tube so that the stopper is properly seated on shoulders 32. The shoulders insure that the tube is inserted far enough in the cup such that the tip 20 of the cannula 16 penetrates the resilient closure 36. They also insure that the tube is not inserted too far such that the slot 18 is occluded or the closure 36 contacts the specimen 40.

After penetration of the closure, the liquid is drawn into slot 18, through the cannula 16, and into the evacuated tube 38. There is virtually no chance of spillage, and a convenient receptacle for storage is provided. The tube is then withdrawn from the cannula and cup, the closure automatically resealing itself. The liquid can then be transferred to a laboratory for testing.

FIG. 6 illustrates another embodiment of the invention, in which the molded plastic container 121 has been filled with a liquid specimen 132 such as urine. The container well 130 is filled up to guide line and stop 125 via entry funnel 131. This level corresponds to a known volume of specimen.

A hollow cannula 122 with a pointed top end 123 is affixed by any suitable means to the base of the container at 126. In this example, the cannula has been epoxied to the base. A slot 124 near the bottom end of the cannula 122 provides access for the liquid's entry into the hollow conduit, and a sleeve 133 of resilient material protects the pointed tip 123 while not in use.

Figure 7:
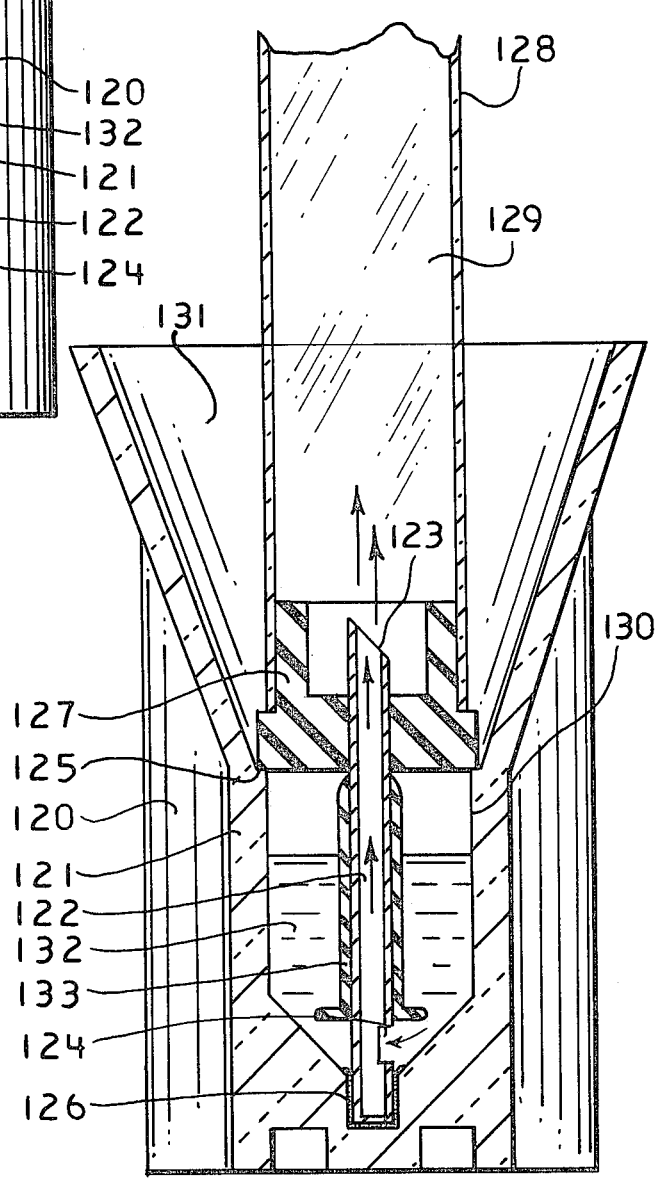
FIG. 7 is a sectional elevation view of the transfer of liquid from the embodiment of FIG. 6 to an evacuated tube.

FIG. 7 shows the operation of the apparatus 121 when used in conjunction with an evacuated glass tube 128. After the well 130 has been filled to the desired level, it is placed on a rigid surface, such as a table, in an upright position as shown. Additional support is gained through having supporting ribs 120.

The evacuated glass tube 128 is stoppered with a rubber or other resilient closure 127, and contains the proper additive to be mixed with the liquid specimen. It is placed into the apparatus through funnel 131 and pushed to stop 125. This insures the penetration of cannula 122 through stopper 127 at point 123 in order that the cannula will enter the interior 129 of the tube 128. The sleeve 133 is displaced downward towards the slot 124, but never to occlude the slot.

To allow for the passage of atmospheric air, allowances (not shown) are made at the interface where the stopper 127 meets the stop 125. Towards this end, either the stop or stopper may contain ribs or undulations so that an air-tight seal at their interface is avoided.

Once the cannula has penetrated the interior of the evacuated tube, the pressure differential created by the tube vacuum and the atmospheric pressure will draw the liquid through slot 124, hollow cannula 122, and into chamber 129. The tube 128 is withdrawn once the sample has been collected, and resilient stopper 127 assumes its normal shape once it has been separated from the cannula. As a result, leakage cannot occur from the tube.

It can be seen that other structures and designs of the specimen sampler cup can be manufactured without departing from the spirit of the invention. The cannula may be secured in different locations and by alternative means, and any means of access for the liquid to enter the hollow conduit will suffice. The device may be used in conjunction with a number of liquids, and can be constructed from any suitable material. The above description and drawings are accordingly intended to be illustrative, and not limiting.

What is claimed is:

1. A liquid specimen collection apparatus for biological fluids comprising:
   a collection container having a closed bottom end and an open top end; and
   a hollow cannula substantially vertically attached to said container, the cannula having an upper end adapted for piercing a closure of an evacuated container, and an opening towards its bottom end in fluid communication with the interior of the collection container
   whereby a liquid deposited in the collection container will flow into the opening towards the bottom end of the cannula, through the cannula, and into the evacuated container when the upper end of the cannula penetrates the closure of the evacuated container.

2. The invention as described in claim 1 wherein the open end of the collection container is wider than the closed end.

3. The invention as described in claim 1 wherein the open end of the collection container is funnel-shaped.

4. The invention as described in claim 1 wherein the cannula is secured to the bottom of the collection container and centrally located therein.

5. The invention as described in claim 1 wherein the collection container has ribs extending into its interior for guidance of the evacuated container.

6. The invention as described in claim 5 wherein the ribs have shoulder portions upon which the evacuated container rests, the shoulders positioned on the ribs at a point higher than the opening towards the bottom end of the cannula, such that placement of the evacuated container within the collection container will not occlude said opening.

7. The invention as described in claim 1 wherein the closed bottom end of the collection container is raised by wall portions contiguous with the walls of the container, the bottom end of the cannula extending beneath the bottom end of the collection container, and a hub portion extending beneath the bottom end of the collection container for supporting the cannula.

8. The invention as described in claim 7 wherein the hub extending below the bottom of the collection container is supported by ribs extending from the hub to the walls of the container.

9. The invention as described in claim 7 wherein a second hub portion extends from the bottom end of the collection container towards the top of the container, the second hub also supporting the cannula.

10. The invention as described in claim 1 wherein the collection container is tapered inwardly from its top and to a point approximately half way to its bottom end, there being a shoulder portion extending from the walls of the collection container about the point at which the taper ends, the cannula being located within the collection container and positioned approximately at its center, the upper end of the cannula extending above the shoulder portion and the opening within the cannula towards its bottom end located below the shoulder portion, whereby the evacuated container, when inserted within the collection container so as to rest upon the shoulder portion, is pierced through its closure by the cannula.

11. The invention as described in claim 10 wherein means are provided at the interface between the shoulder portion and the evacuated container to allow the passage of atmospheric air.

12. The invention as described in claim 10 wherein ribs are provided on the exterior of the collection container for stability.

13. The apparatus as described in claim 1 wherein the collection container is of molded platic.

14. The invention as described in claim 1 wherein a sleeve is provided for covering the upper end of the cannula when the apparatus is not in use.

15. The invention as described in claim 14 wherein the sleeve is resilient, and is adapted to be displaced towards the bottom of the cannula as the upper end of said cannula penetrates the closure of an evacuated container.

* * * * *

UNITED STATES PATENT AND TRADEMARK OFFICE
CERTIFICATE OF CORRECTION

PATENT NO. : 4,116,066
DATED : September 26, 1978
INVENTOR(S) : Jack J. Mehl and Edward L. Nugent It is certified that error appears in the above-identified patent and that said Letters Patent are hereby corrected as shown below:

At Column 1, line 10, - "or" should be -- of --;

At Column 1, line 16, - "shoud" should be -- should --;

At Column 1, line 27, - "liquiid" should be -- liquid --;

At Column 1, line 33, - "openig" should be -- opening --;

At Column 4, Claim 13, line 51, - "platic" should be -- plastic --.

Signed and Sealed this

Twentieth Day of February 1979

[SEAL]

Attest:

RUTH C. MASON
Attesting Officer

DONALD W. BANNER
Commissioner of Patents and Trademarks